United States Patent
Gertz et al.

(10) Patent No.: US 8,961,502 B2
(45) Date of Patent: Feb. 24, 2015

(54) DEVICE FOR IRRADIATING AN INTERNAL BODY SURFACE

(75) Inventors: David Gertz, Jerusalem (IL); Lilach Gavish, Mevasseret Zion (IL); Petachia Reissman, Jerusalem (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 1519 days.

(21) Appl. No.: 12/296,221

(22) PCT Filed: Apr. 10, 2007

(86) PCT No.: PCT/IL2007/000448
§ 371 (c)(1),
(2), (4) Date: Jun. 1, 2009

(87) PCT Pub. No.: WO2007/113834
PCT Pub. Date: Oct. 11, 2007

(65) Prior Publication Data
US 2009/0287194 A1   Nov. 19, 2009

(30) Foreign Application Priority Data
Apr. 6, 2006   (IL) .......................................... 174858

(51) Int. Cl.
*A61B 18/18* (2006.01)
*A61B 18/24* (2006.01)
*A61N 5/06* (2006.01)
*A61B 18/22* (2006.01)

(52) U.S. Cl.
CPC .............. *A61B 18/24* (2013.01); *A61N 5/0603* (2013.01); *A61B 2018/2261* (2013.01)
USPC ............................................................. 606/8

(58) Field of Classification Search
USPC ....................... 606/3, 8, 9, 11, 12; 607/88, 89
See application file for complete search history.

(56) References Cited

U.S. PATENT DOCUMENTS 4,643,186 A  *  2/1987  Rosen et al. .................... 606/33
4,961,738 A  *  10/1990  Mackin ............................ 606/15
4,998,930 A  *  3/1991  Lundahl .......................... 606/15

(Continued)

FOREIGN PATENT DOCUMENTS

EP    1527798 A    5/2005
WO    2005/049127 A    6/2004

OTHER PUBLICATIONS

Lilach Gavish, et al. "Low-level laser irradiation inhibits abdominal aortic aneurysm progression in apolipoprotein E-deficient mice", Cardiovascular Research (2009) 83, 785-792, European Society of Cardiology, 2009.

(Continued)

*Primary Examiner* — Tuan V Nguyen
(74) *Attorney, Agent, or Firm* — Kilpatrick Townsend & Stockton LLP (57) ABSTRACT

The invention provides a device and method for illuminating a body surface. A light source is optically coupled to the proximal end of a light guide and a light scatterer is optically coupled to the distal end of the light guide. The device includes a deployment mechanism that is configured to bring the light scatterer from a small caliber configuration in which the light scatterer is delivered to the body surface to a large caliber configuration in which the light scatterer irradiates the body surface. The invention may be used, for example, irradiate the periadventitial surface of an aneurysmal blood vessel.

21 Claims, 7 Drawing Sheets

(56) References Cited

U.S. PATENT DOCUMENTS

| | | | |
|---|---|---|---|
| 5,163,950 A * | 11/1992 | Pinchuk et al. | 606/192 |
| 5,344,419 A | 9/1994 | Spears | |
| 6,071,302 A | 6/2000 | Sinofsky | |
| 6,159,236 A * | 12/2000 | Biel | 607/92 |
| 6,814,733 B2 * | 11/2004 | Schwartz et al. | 606/41 |
| 7,860,555 B2 * | 12/2010 | Saadat | 600/476 |
| 2008/0004686 A1 | 1/2008 | Hunt et al. | |
| 2008/0208297 A1 | 8/2008 | Gertner et al. | |

OTHER PUBLICATIONS

International Search Report issued Jul. 18, 2007, pp. 1-4.
Office Action mailed Dec. 8, 2014, from U.S. Appl. No. 13/836,273 (14 pages).

* cited by examiner

DEVICE FOR IRRADIATING AN INTERNAL BODY SURFACE

FIELD OF THE INVENTION

This invention relates to medical devices and more specifically to such devices for internal irradiation of the body.

BACKGROUND OF THE INVENTION

Application of light to a tissue surface has been used in several medical treatments. For example, it is known to apply light to a tissue surface in order to heal a pathological state, to remove a stenosis in a blood vessel or for laser welding of tissues, for example in order to treat a rupture in a vessel wall or to perform an anastomosis of two blood vessels. It is also known to use application of light for tissue regeneration and therapy. For example low level laser irradiation in the visible to far-red range of the light spectrum has been shown clinically to accelerate wound healing in skin wounds, and reduce pain and inflammation in musculoskeletal disorders. The underlying mechanisms are initiating (biostimulating) processes such as collagen synthesis, cell proliferation, and reducing secretion of inflammatory markers. Gavish et al., *Lasers in Surgery and Medicine* (2006) 38:779-786, which is incorporated herein by reference, discloses that low level laser in vitro stimulates vascular smooth muscle cell proliferation and collagen synthesis, modulates the equilibrium between regulatory matrix remodeling enzymes, and inhibits pro-inflammatory IL-1-$\beta$ gene expression.

U.S. Pat. No. 7,051,738 to Oron et al discloses an apparatus for applying light to the heart tissue for a biostimulative and cytoprotective effect. U.S. Pat. No. 5,370,608 to Sahota et al discloses a light angioplasty catheter for exposing the vessel wall to light from an intravascular approach for the prevention of restenosis.

U.S. Pat. No. 7,108,692 to Frenz et al discloses an apparatus for applying light to the interior surface of a vessel wall for laser welding of two vessels. Light generated by an extracorporeal light source is guided to the interior of the blood vessel to be treated by a light guide. A light deflector directs the light in a substantially radial fashion onto the vessel wall.

Abdominal Aortic Aneurysm (AAA) formation is an arteriosclerotic process characterized by marked disruption of the musculoelastic lamellar structure of the media. Extensive destruction of the elastic tissue is associated with marked inflammatory cell infiltration and progressive diminution in the number of viable smooth muscle cells. With time, and aggravated by contributory risk factors such as systolic hypertension, aneurysm growth occurs through a complicated, but insidious, imbalance between matrix protein production and degradation, favoring expansion, thereby increasing the risk of rupture of the weakened wall.

AAA is present in approximately 10% of individuals over the age of 65 years, with its frequency increasing as the proportion of elderly individuals in the general population continues to rise. It is widely known that the risk of rupture increases in approximate proportion to aneurysm size, which can be monitored by computed tomography (CT), ultrasound, or magnetic resonance imaging (MRI). The estimated risk of rupture ranges from 10-20% for an abdominal aneurysm 6-7 cm in diameter, to 30-50% if the maximum diameter is greater than 8 cm. Overall mortality from a ruptured AAA is greater than 90%.

Current forms of aneurysm treatment focus either on the open abdomen, surgical, graft-based repair or endovascular exclusion of the diseased segment of aorta with large, membrane-covered, e.g. Gortex covered stents. Both techniques have major side effects with potentially life-threatening consequences, particularly in patients of advanced age (the majority of patients) or others at high risk or compromised cardiac function.

SUMMARY OF THE INVENTION

In its first aspect, the present invention provides a device for illuminating a tissue surface. The device of the invention may be used to radiate a tissue surface, for example, for treatment of an aneurysm, tissue welding, or removal of a stenosis in a blood vessel. The illuminating device of the invention has a slender shaft that may be rigid or flexible, as required in any application. Light is irradiated from the distal end of the shaft. In one preferred embodiment, the shaft is connected at its proximal end to a light source, that may be, for example, a laser. Light generated by a light source at the proximal end of the shaft is conducted through the shaft via a light guide to the distal end of the shaft. Alternatively, a light source, such as a light emitting diode (LED) may be positioned at the distal end of the shaft. A light scatterer is positioned at the distal end of the shaft that is optically coupled to the light guide. Light emerging from the distal end of the light guide is scattered by the light scatterer so that light emerges from the light scatter from an illuminating surface having an area that is larger than the cross-sectional area of the light guide The illuminating surface is transformable between an undeployed, small caliber configuration in which it is delivered to the tissue surface to be treated, and a deployed, large caliber configuration in which the treatment is delivered. In the deployed configuration, the illuminating surface is preferably shaped to conform to the surface to be radiated so that the illuminating surface can be applied onto the surface to be radiated. For example, for illuminating the perivascular (adventitial) surface of a blood vessel, the deployed illuminating surface would preferably have a partial cylindrical surface. As explained below, this enhances coupling and homogeneity of the light radiated from the illuminating surface and radiation of the surface to be treated. At the conclusion of the treatment, the illuminating surface is brought to its small caliber undeployed configuration, and the device is removed from the body.

The illuminating device of the invention may be provided with means for firmly attaching the deployed illuminating surface to the tissue surface to be treated. Such means may comprise, for example, use of suction or attachment hooks.

The light source is selected in accordance with the requirements of the particular application. For example, in order to treat an aneurysm, low level laser irradiation (also known as "low energy laser", "photo-biostimulation" and "red-light therapy") in the range of 500 to 900 nm, and more preferably in the range of 600 to 900 nm, may be used that is preferably emitted from the illuminating surface with an energy flux in the range of about 0.01 to about 50 Joules/cm$^2$, and more preferably from about 0.1 to about 5 Joules/cm$^2$. For surgical welding, light in the 780 to 2010 nm range may be used, in which case the light source may be a semiconductor diode laser that generates 808 nm light or a diode-pumped Ho:YAG laser which generates 2010 nm light.

In its second aspect, the invention provides a method for treating a tissue surface. In accordance with this aspect of the invention, the distal end of the illuminating device of the invention is delivered, with the light illuminating surface in its undeployed configuration to the body site to be treated. The light illuminating surface is then brought to its deployed configuration and is applied to the surface to be treated, and the surface to be treated is radiated. At the conclusion of the radiation, the light illuminating surface is removed from the body surface and the light illuminating surface is brought into its undeployed configuration and the device is removed from the body.

The device and method of the invention may be used for illuminating the perivascular surface of a blood vessel, for example, in order to treat an aneurysm. Without wishing to be bound by a particular theory, it is believed that irradiating an aneurysmal blood vessel with low level laser irradiation retards progression of the aneurysm by bio-stimulating the vessel wall to produce extracellular matrix and reduce inflammation.

Thus, in its first aspect, the invention provides a device for illuminating a body surface, comprising:
  (a) a shaft having a proximal end and a distal end, the shaft including a light guide having a cross-sectional area and guiding light from the proximal end to the distal end;
  (b) a light source optically coupled to the proximal end of the light guide;
  (c) a light scatterer optically coupled to the distal end of the light guide, the light scatterer having a small caliber configuration and a large caliber configuration, and further having an illuminating surface having an area greater than the cross sectional area of the light guide; and
  (d) a deployment mechanism configured to bring the light scatterer from the small caliber configuration to the large caliber configuration.

In its second aspect, the invention provides a method for illuminating a body surface, comprising:
  (a) providing a device for illuminating the body surface, the device comprising:
    a shaft having a proximal end and a distal end, the shaft including a light guide having a cross-sectional area and guiding light from the proximal end to the distal end;
    a light source optically coupled to the proximal end of the light guide;
    a light scatterer optically coupled to the distal end of the light guide, the light scatterer having a small caliber configuration and a large caliber configuration, and further having an illuminating surface having an area greater than the cross sectional area of the optic fiber; and
    a deployment mechanism configured to bring the light scatterer from the small caliber configuration to the large caliber configuration
  (b) delivering the distal end of the shaft to the body surface with the light scatterer in the small caliber configuration;
  (c) activating the deployment mechanism to bring the light scatterer into the large caliber configuration;
  (d) applying the illuminating surface to the body surface; and
  (e) illuminating the body surface from the light source.

In its third aspect, the invention provides a method for treating an aneurysmal blood vessel comprising irradiating the blood vessel with radiation having a wavelength from 500 to 900 nm.

In its fourth aspect, the invention provides a device for illuminating a body surface, comprising:
  (a) an elongated shaft having a proximal end and a distal end, the shaft including a light guide having a cross-sectional area and guiding light from the proximal end to the distal end;
  (b) a light source optically coupled to the proximal end of the light guide and illuminating light having a wavelength in the range of 500 to 900 nm; and
  (c) a light scatterer optically coupled to the distal end of the light guide.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 shows a device for illuminating a tissue surface in accordance with one embodiment of the invention;

FIG. 2 shows a device for illuminating a tissue surface in accordance with a second embodiment of the invention;

FIG. 3 shows a device for illuminating a tissue surface in accordance with a third embodiment of the invention; and FIG. 4 shows use of the device of the invention for treating an aneurysm.

DETAILED DESCRIPTION OF EMBODIMENTS

FIG. 1 shows a device, generally indicated by 10, for illuminating a tissue surface to be treated, in accordance with one embodiment of the invention. The tissue surface may be, for example, the outer surface of a blood vessel where an aneurysm has formed. The illuminating device has a slender shaft 11, shown in longitudinal section in FIG. 1, having a proximal end 15 and a distal end 17. The shaft 11 may be rigid or flexible, as required in any application. The shaft 11 has a sheath 13 surrounding a light guide 20 that may consist of a single optical fiber or a bundle of optical fibers. The optical fiber is typically made from glass.

Figure 1A:
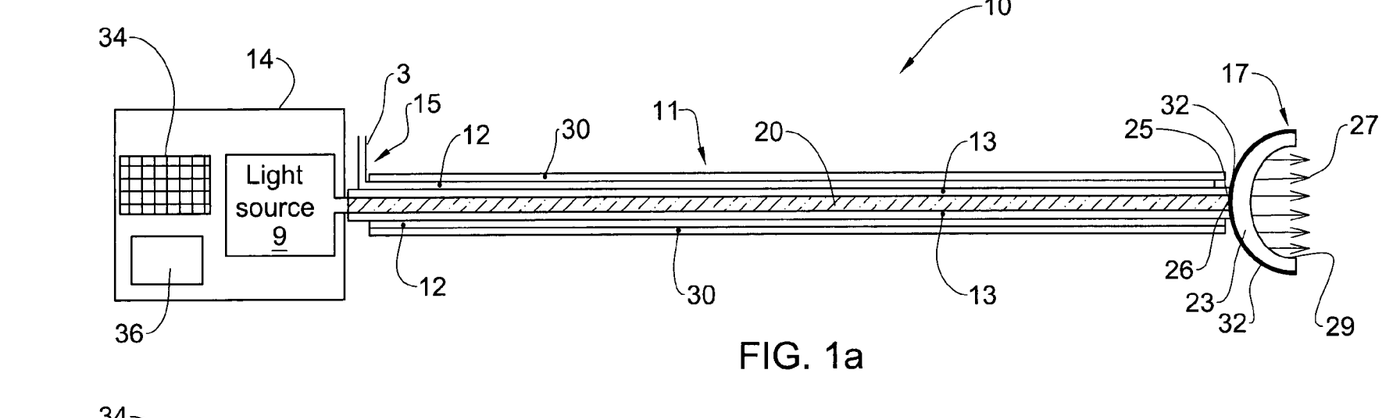

The shaft 11 is connected at its proximal end 15 to a control unit 14 that houses a light source 9, that may be, for example, a laser. Light generated by the light source 9, enters the light guide 20 and is conducted through the light guide 20 to the distal end of the light guide 20. Since the end face 26 of the distal end of the light guide 20 is flat, the pencil of light emerging from the end face 26 will have a cross-sectional area essentially equal to the cross-sectional area of the light guide 20. Thus, in accordance with the invention, in order to increase the radiated area, the radiation device 10 further comprises a light scatterer 23 positioned at the distal end of the light guide 20, that is optically coupled to the light guide 20. The light scatterer 23 has a deployed configuration shown in FIG. 1a in which an illuminating surface 29 has a large caliber. Light emitted from the end face 26 of the light guide 20 enters the light scatterer 23 at a first surface 25 and is scattered through the light scatterer 23. The light is then emitted from the illuminating surface 29, as indicated by the arrows 27 to radiate the site to be treated, as described below. The illuminating surface has an area that is greater than the cross-sectional area of the light guide 20. In the deployed configuration, the illuminating surface 29 is preferably shaped to conform to the surface to be radiated so that the illuminating surface can be applied onto the surface to be radiated. For example, for illuminating the outer surface of a blood vessel, the illuminating surface 29 would be a partial cylindrical surface, as shown in FIG. 1a. As explained below, this enhances coupling of the light radiated from the illuminating surface and radiation of the surface to be treated. The light scatterer is preferably provided with a light reflecting coating 32 on its rear surface in order to reflect back scattered light in the light scatterer in the direction of the arrows 27.

Figure 1B:
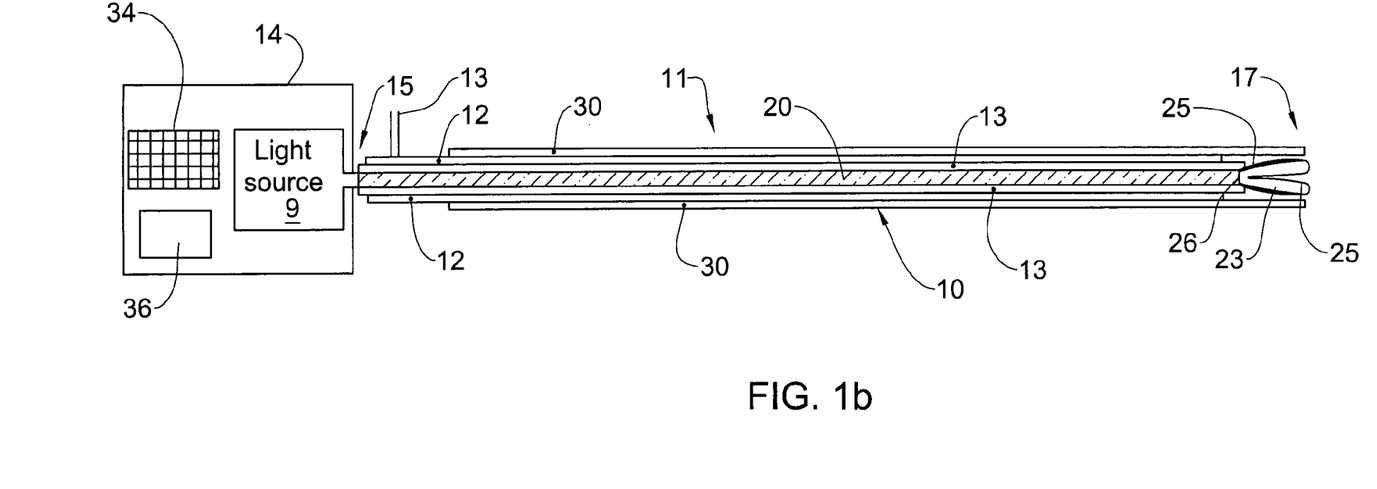

The light scatterer 23 also has an undeployed configuration shown in FIG. 1b in which the illuminating surface 29 is collapsed into a small caliber. In the embodiment shown in FIG. 1, the light scatterer 23 is formed from a resiliently flexible material. The light scatterer may be made, for example, from transparent silicon rubber in which a light scattering substance is embedded. Alternatively, the light scatter may include one or more lenses (not shown). In this embodiment, the shaft 11 includes a constraining sleeve 30 that surrounds the sheath 13. In the undeployed configuration shown in FIG. 1b, the light scatterer 23 is constricted into its small caliber undeployed configuration and is maintained in the undeployed configuration by means of the constraining sleeve 30. The constraining sleeve 30 is slidable axially along the shaft 11 from a forward position shown in FIG. 1b and a rearward position shown in FIG. 1a. In the forward position (FIG. 1b), the sleeve 30 extends beyond the end of the optic fiber 20 with the light scatterer 23 collapsed in the interior of the sleeve 30. When the sleeve 30 is brought to its rearward position (FIG. 1a) the sleeve 30 is retracted from the light scatterer 30 and the light scatterer 23 spontaneously assumes its deployed, large caliber configuration due to the resiliently flexible character of the light scatterer 23. In order to slide the sleeve 30 between its forward and rearward position, a user may grasp the sleeve 30 at its proximal end and manually slide the sleeve over the sheath 13.

The illuminating device 10 may further be configured for connection to a source of negative pressure. As shown in FIG. 1, for this purpose, the shaft may include a channel 12 extending from a valve 3 adapted for connection to a source of negative pressure (not shown) at the proximal end of the shaft 11 through the shaft 11 to the distal end of the shaft. As explained below, generation of negative pressure at the distal end of the light scatterer 23 is used to attach the light scatterer 23 to the tissue surface and to immobilize the light scatterer on the tissue surface during radiation.

The shaft 11 may optionally contain a working channel (not shown) in order to accommodate a guide wire or working tool, as required in any application.

The control unit 14 is provided with a user input device, such as a keypad 34 to allow the user to select one or more parameters of the treatment, such as the radiation intensity or fluency. The control unit may also have a display 36 such as a screen 38 displaying the selected parameters and other relevant information.

Figure 2A:
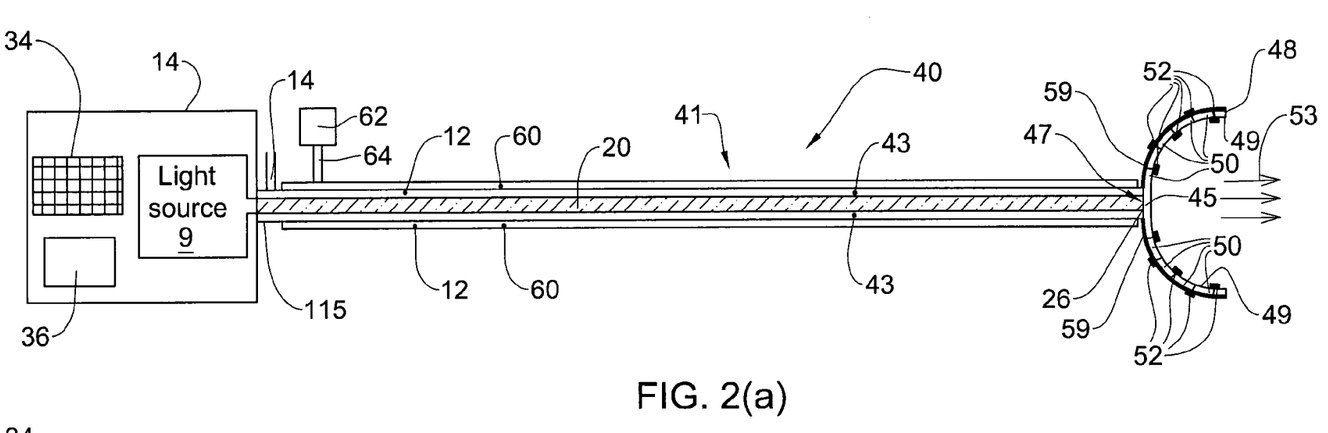
Figure 2B:
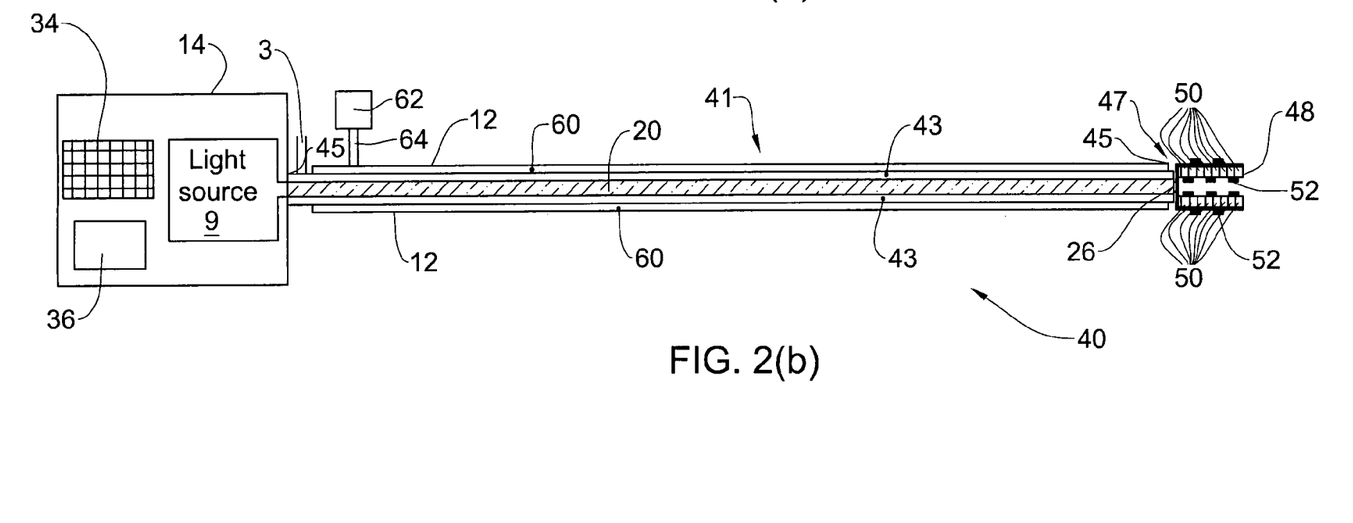

FIG. 2 shows a device, generally indicated by 40, for illuminating a tissue surface to be treated, in accordance with another embodiment of the invention. The tissue illuminating device 40 has several components in common with the device 10 described above in reference to FIG. 1, and similar components are indicated by the same reference numerals in FIGS. 1 and 2 without further comment. The illuminating device has a slender shaft 41, shown in longitudinal section in FIG. 2, having a proximal end 45 and a distal end 47. The shaft 41 may be rigid or flexible, as required in any application. The shaft 41 has a sheath 43 surrounding a light guide 20 that may consist of a single optical fiber or a bundle of optical fibers.

The device 40 includes a light scatterer 48 at the distal end 47 of the shaft that is optically coupled to the light guide 20. The light scatterer 48 has a large caliber deployed configuration shown in FIG. 2a, and a small caliber undeployed configuration shown in FIG. 2b. In this embodiment, the light scatterer 48 includes a pleated sheet containing two or more panels 50 that are hinged together by hinges 52. In the undeployed configuration (FIG. 2b) the pleated sheet is folded into the small caliber, while in the deployed configuration (FIG. 2a) the pleated sheet is extended. The panels may be formed from transparent silicone rubber in which a light scattering substance is embedded. Light emitted from the end face 26 of the light guide 20 enters the light scatterer 48 at a first surface 45 and is scattered through the light scatterer 48. The light is then emitted from an illuminating surface 49 on each panel in an essentially forward direction, as indicated by the arrows 53 to radiate the site to be treated. In the deployed configuration, the illuminating surface 49 is preferably shaped to conform to the surface to be radiated so that the illuminating surface can be applied onto the surface to be radiated. The light scatterer is preferably provided with a light reflecting coating 59 on its rear surface in order to reflect back scattered light in the light scatterer in the direction of the arrows 53. The reflecting coating 59 may be made, from a biocompatible shiny material, deposited on the rear surface of the light scatterer.

The light scatterer 48 further includes an actuating mechanism for transforming the light scatterer 48 between its deployed and undeployed configurations. The hinges 52 comprise one or more elements formed from a shape memory material such as Nitinol that has been trained to behave as described below. The hinges have a deployed configuration shown in FIG. 2a, and an undeployed configuration shown in FIG. 2b. The hinges are attached to the panels so that passage of the elements from their undeployed to their deployed configurations drives the passage of the light scatterer 48 between its undeployed configuration and its deployed configuration, and vice versa.

The shaft 41 has a channel 60 for delivering a pressurized liquid such as physiological saline from a fluid source 62 located adjacent to, or inside, the control unit 14. The fluid source 62 includes a temperature controlling system that allows the temperature of the fluid to be selected by a user. The fluid source 62 is in fluid contact with the channel 60 via a connecting hose 64. When the light scatterer 48 in its undeployed configuration is to be brought to its deployed configuration, a pressurized fluid is used at a first temperature. The fluid is delivered to the distal end 47 of the shaft where it brings the temperature of the hinge elements to a temperature at which the shape memory material undergoes a first shape transition bringing the hinges 52 into their deployed configuration. When the light scatterer 48 in its deployed configuration is to be brought to its undeployed configuration, a pressurized fluid is used at a second temperature that is delivered to the distal end of the shaft where it brings the temperature of the hinges 52 to a temperature at which the shape memory material undergoes a second shape transition bringing the hinges 52 into their undeployed configuration.

Figure 3A:
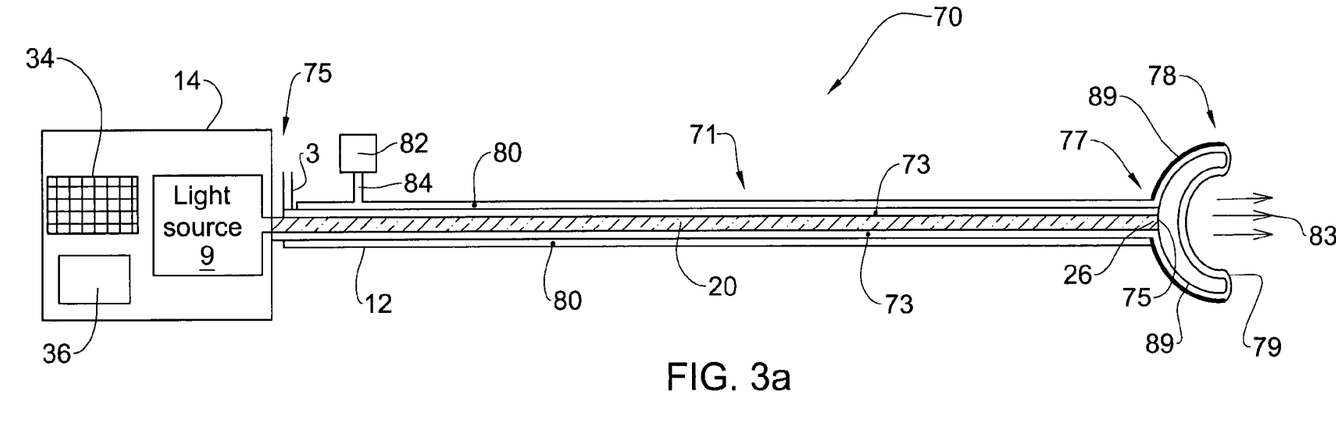
Figure 3B:
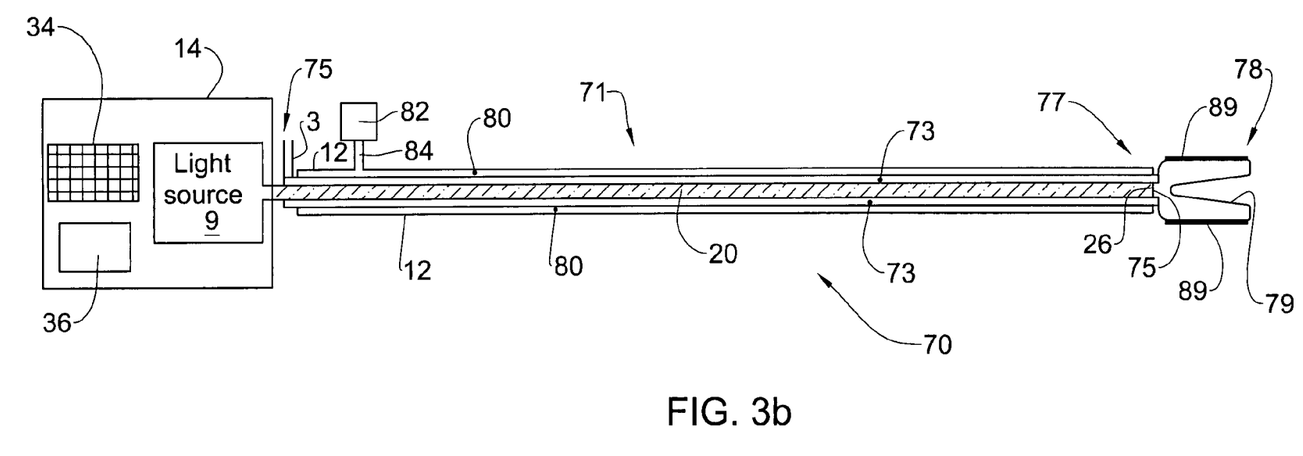

FIG. 3 shows a device, generally indicated by 70, for illuminating a tissue surface to be treated, in accordance with yet another embodiment of the invention. The tissue illuminating device 70 has several components in common with the device 10 described above in reference to FIG. 1, and similar components are indicated by the same reference numerals in FIGS. 1 and 3 without further comment. The illuminating device has a slender shaft 71, shown in longitudinal section in FIG. 3, having a proximal end 75 and a distal end 77. The shaft 71 may be rigid or flexible, as required in any application. The shaft 71 has a sheath 73 surrounding a light guide 20 that may consist of a single optical fiber or a bundle of optical fibers.

The device 70 includes a light scatterer 78 at the distal 77 of the shaft that is optically coupled to the light guide 20. In this embodiment, the tight scatterer 78 is an inflatable balloon that may be formed, for example, from transparent silicone rubber in which a light scattering substance is embedded. The light scatterer 78 has a large caliber deployed configuration shown in FIG. 3a in which the balloon is inflated, and a small caliber undeployed configuration shown in FIG. 3b in which the balloon is deflated. In the deployed configuration, light emitted from the end face 26 of the light guide 20 enters the light scatterer 78 at a first surface 75 and is scattered through the light scatterer 78. The light is then emitted from an illuminating surface 79 of the light scatterer 78 in an essentially forward direction, as indicated by the arrows 83 to radiate the site to be treated. In the deployed configuration, the illuminating surface 79 is preferably shaped to conform to the surface to be radiated so that the illuminating surface can be applied onto the surface to be radiated. The light scatterer is preferable provided with a light reflecting coating 89 on its rear surface in order to reflect back scattered light in the light scatterer in the direction of the arrows 83.

The shaft 71 has a channel 80 for delivering a pressurized fluid such as water or air from a fluid source 82 located adjacent to, or inside, the control unit 14. The fluid source 82 is in fluid contact with the channel 80 via a connecting hose 84. When the light scatterer 78 in its undeployed configuration is to be brought to its deployed configuration, the pressurized fluid is delivered to the distal end 47 of the shaft and inflates the balloon. When the light scatterer 78 in its deployed configuration is to be brought to its undeployed configuration, the fluid is pumped from the balloon back to the fluid source 82.

FIG. 4 depicts use of the device 40 in a surgical procedure in which an internal body surface is to be radiated. In the example of FIG. 4, the surgical procedure is treatment of an aneurysm in the abdominal aorta 102. This is by way of example only, and the device of the invention may be used to radiate any body surface. As shown in FIG. 4*a*, the shaft 41 of the device 40, with the light scatterer 48 in its undeployed configuration, is introduced through an incision at a first location 96 on the body surface of a subject 95 into a body cavity, which in this example, is an abdomen 99. The surgical procedure may utilize laparoscopy, in which case an endoscope 97 is introduced into the abdomen 99 through a second incision at a second location 98 on the body surface. Abdominal body organs (not shown in FIG. 4) are moved aside in order to allow access to the aorta 102. The endoscope 97 illuminates the abdomen 99 including the outer surface of the aorta 102. The endoscope 97 is part of a laparoscopic imaging system that displays on a display screen (not shown), an image of the abdomen 99, so as to allow a user 110 to observe the cavity 99 during the procedure. The abdomen 99 may temporarily be expanded in order to facilitate the maneuverability of the device 40 and the endoscope 97 in the abdomen 99.

Figure 4A:
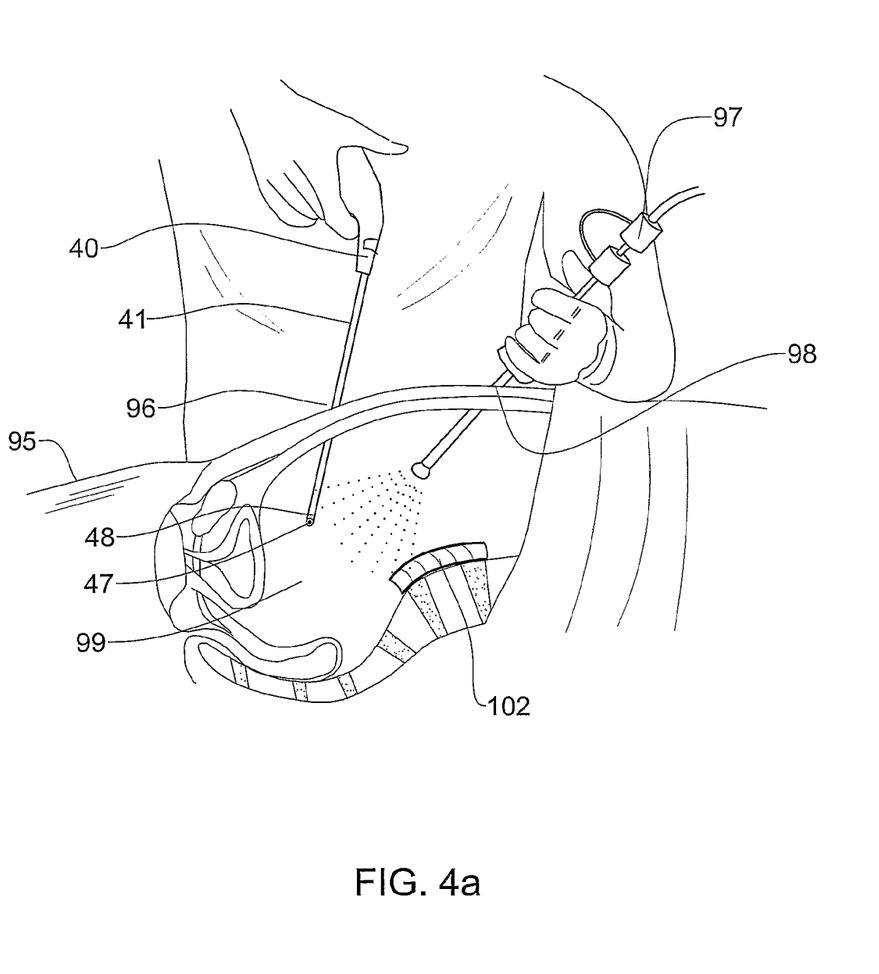
Figure 4B:
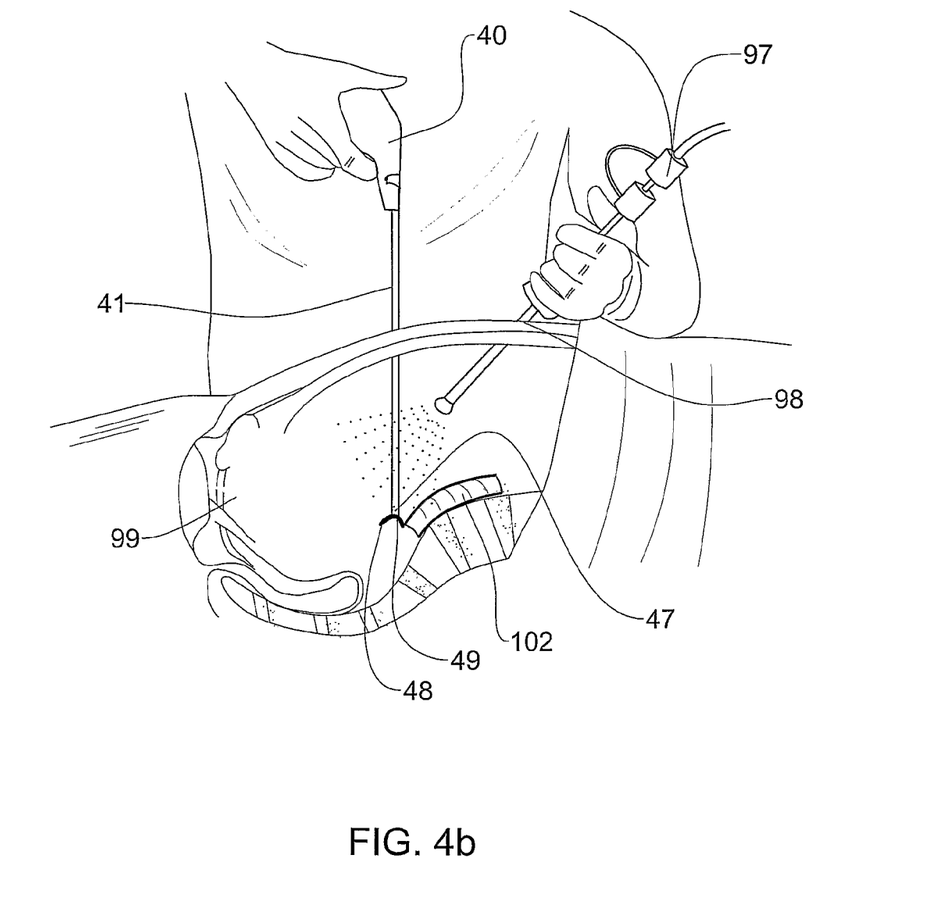
Figure 4C:
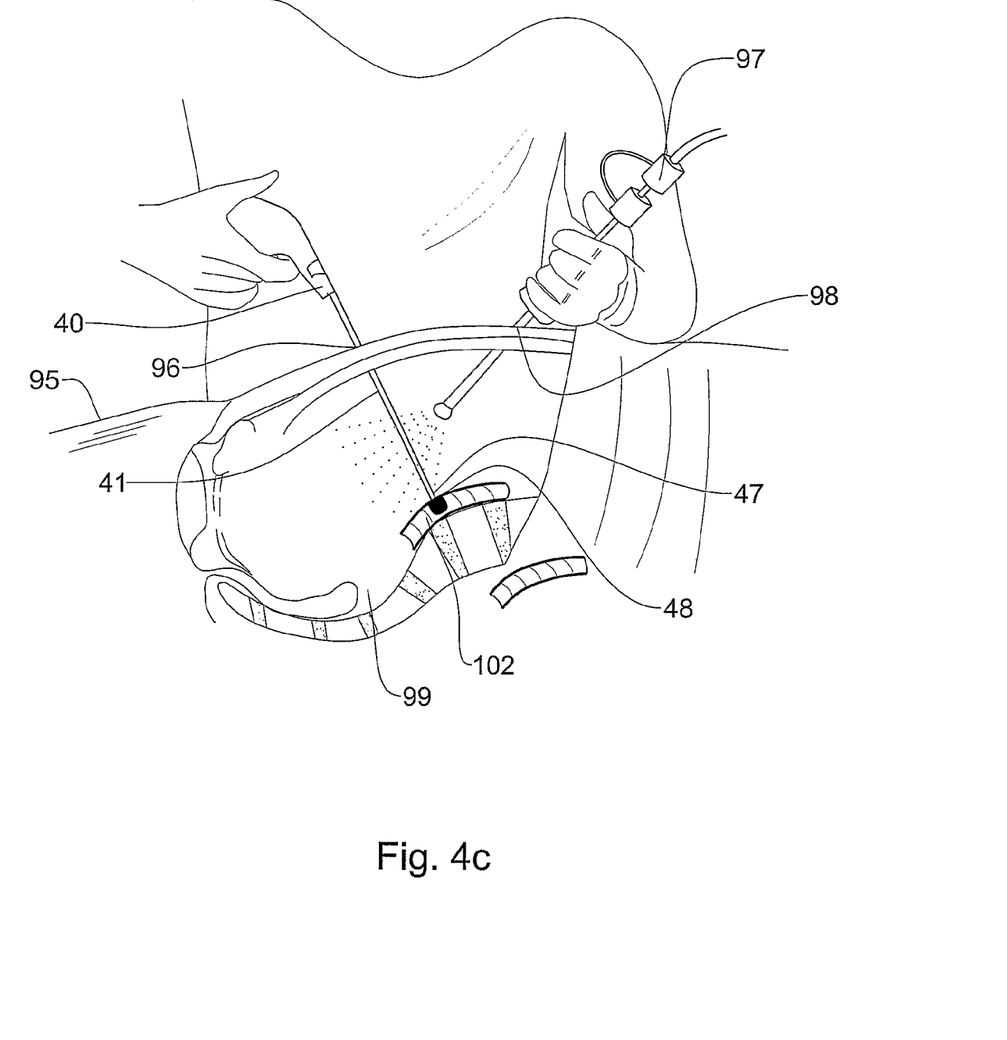

In FIG. 4*a*, the device 40 has been maneuvered so as to bring the distal end 47 of the shaft 41 and the light scatterer 48 into proximity with the aorta 102. At this point, the fluid in the fluid source 62 (FIG. 2) is brought to the first temperature and the fluid source 62 is then activated in order to deliver the fluid at the first temperature through the connecting hose 64 (FIG. 2) and the channel 60 (FIG. 2) to the distal end 47 of the shaft where it brines the hinge elements to a temperature in which they assume their deployed configuration. This brings the light scatterer 48 to its deployed configuration, as shown in FIG. 4*b*. The illuminating surface 49 of the light scatterer 48 in the deployed configuration of the light scatterer 48 has the shape of a partial cylindrical surface with a radius approximately equal to the outer radius of the aorta 102 to be radiated. The device 40 is then maneuvered in the abdomen 99 so as to apply the illuminating surface 49 to the outer surface of the aorta 102, as shown in FIG. 4*c*. The valve 3 is then opened to deliver negative pressure to the light scatterer 48 so as to firmly apply the illuminating surface 49 to the aorta and to immobilize the light scatterer 48 on the outer surface of the aorta. The light source in the control unit 14 is then activated. Light from the light source is conducted along the light guide 20 to the light scatterer 48. Essentially the entire surface area of the aorta that is in contact with the illuminating surface 49 is simultaneously radiated.

Figure 4D:
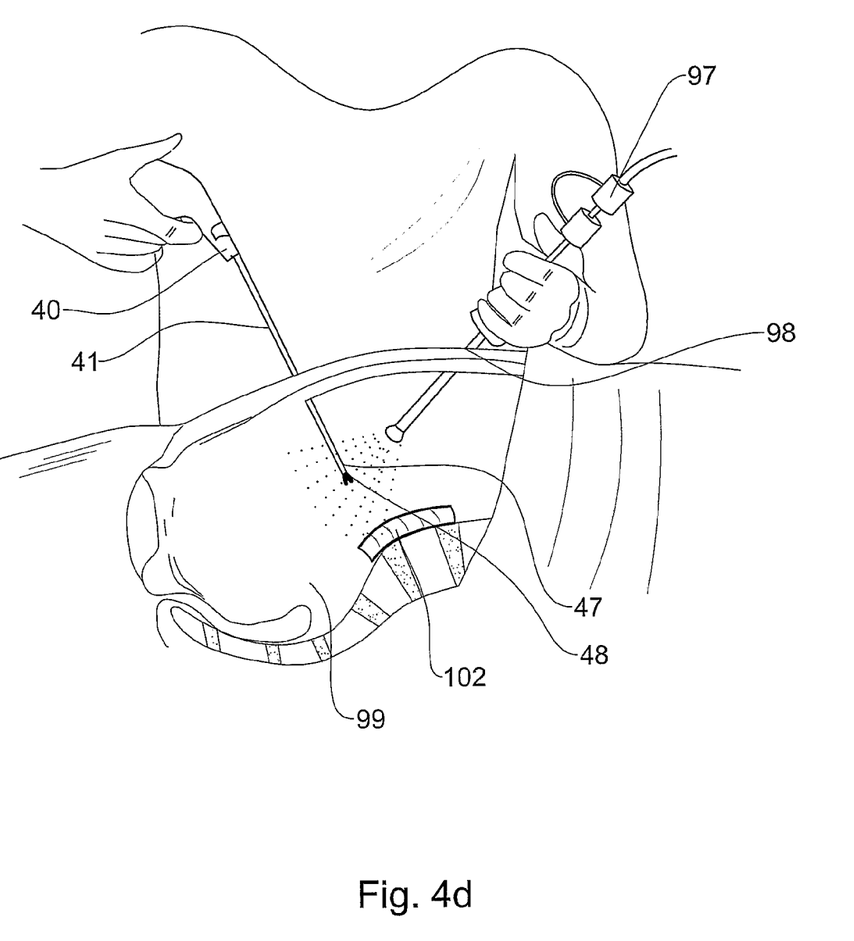

When the radiation is completed, the negative pressure is discontinued to release the light scatterer 48 from the aorta. The fluid in the fluid source 62 is brought to the second temperature, and the fluid source 62 is then activated in order to deliver the fluid at the second temperature through the connecting hose 64 and the channel 60 to the distal end 47 of the shaft where it brings the hinge elements to a temperature in which they assume their undeployed configuration. This brings the light scatterer 48 back to its undeployed configuration, as shown in FIG. 4*d*. The device 40 is then removed from the abdomen 99.

The invention claimed is:

1. A device for illuminating a body surface, comprising:
   (a) a shaft having a proximal end and a distal end, the shaft including a light guide having a cross-sectional area and guiding light from the proximal end to the distal end;
   (b) a light source optically coupled to the proximal end of the light guide;
   (c) a light scatterer attached to, and optically coupled to, the distal end of the light guide, the light scatter having a small caliber configuration and a large caliber configuration, and further having in the large caliber configuration a concave illuminating surface and having an area greater than the cross sectional area of the light guide; wherein the light scatterer comprises a reflective surface configured to reflect back scattered light in the light scatterer in a forward direction; and
   (d) a deployment mechanism actuatable to bring the light scatterer from the small caliber configuration to the large caliber configuration, wherein the concave illuminating surface comprises an external facing and concave surface.

2. The device according to claim 1 wherein the deployment mechanism is further configured to bring the light scatterer from the large caliber configuration to the small caliber configuration.

3. The device according to claim 1 wherein the illuminating surface is a concave cylindrical surface.

4. The device according to claim 1 wherein the light source generates light with a wavelength in a range from 500 to 900 nm.

5. The device according to claim 4 wherein the light source has a fluency between 0.01 and 60 Joules/cm$^2$.

6. The device according to claim 3 wherein the light source has fluency between 0.1 and 5 Joules/cm$^2$.

7. The device according to claim 1 wherein the light source generates light with a wavelength in a range from about 780 nm to about 2010 nm.

8. The device according to claim 1 wherein the light scatterer is formed from a resiliently flexible material.

9. The device according to claim 8 wherein the deployment device comprises a sleeve surrounding the shaft, the sleeve being slidable between a first position in which the light scatterer is constrained by the sleeve in the small caliber configuration and a second position in which the light scatterer adapts the large caliber configuration.

10. The device according to claim 1 wherein the light scatterer is inflatable.

11. The device according to claim 10 wherein the deployment mechanism delivers a pressurized fluid to the light scatterer to inflate the light scatterer.

12. The device according to claim 1 wherein the illuminating surface is a pleated sheet.

13. The device according to claim 12 wherein the deployment mechanism comprises elements formed from a shape memory alloy trained to have a first configuration coupled to the large caliber configuration of the light scatterer and a second configuration coupled to the small caliber configuration of the light scatterer.

14. The device according to claim 13 wherein the deployment mechanism further comprises a liquid delivery system delivering a liquid from a source to the light scatter.

15. The device according to claim 14 wherein the deployment mechanism further comprises a temperature controlling system controlling the temperature of the liquid.

16. The device according to claim 1 the illuminating surface configured to forcibly attach to the body surface.

17. The device according to claim 1 adapted for illuminating a perivascular surface of a blood vessel.

18. A device for illuminating a peri-adventitial surface of a blood vessel, comprising:
   (a) an elongated shaft having a proximal end and a distal end, the shaft including a light guide having a cross-sectional area and guiding light from the proximal end to the distal end;
   (b) a light source optically coupled to the proximal end of the light guide and illuminating light having a wavelength in the range of 500 to 900 nm; and
   (c) a light scatterer attached to and optically coupled to the distal end of the light guide having a concave cylindrical surface; wherein the light scatterer has an expanded configuration and an unexpanded configuration, and wherein the concave cylindrical surface comprises an external facing and concave surface; wherein the light scatterer comprises a reflective surface configured to reflect back scattered light in the light scatterer in a forward direction.

19. The device according to claim 18 wherein the light source has a wavelength from 600 to 900 nm.

20. The device according to claim 18 wherein the light source has fluency between 0.001 and 50 Joules/cm$^2$.

21. The device according to claim 18 wherein the light source has fluency between 0.01 and 5 Joules/cm$^2$.

* * * * *